United States Patent
Berry

[11] Patent Number: 5,953,102
[45] Date of Patent: Sep. 14, 1999

[54] METHOD FOR SUBSTANTIALLY OBJECTIVE TESTING OF THE VISUAL CAPACITY OF A TEST SUBJECT

[76] Inventor: Francis D. Berry, 1768 Glendon Ave. #1, Los Angeles, Calif. 90024

[21] Appl. No.: 08/898,972

[22] Filed: Jul. 23, 1997

[51] Int. Cl.$^6$ ........................................................ A61B 3/00
[52] U.S. Cl. ............................................ 351/247; 351/205
[58] Field of Search ........................... 351/205, 222, 351/237, 239, 242, 246, 247

[56] References Cited

U.S. PATENT DOCUMENTS

| | | | |
|---|---|---|---|
| 3,623,799 | 11/1971 | Millodot | 351/205 |
| 3,992,087 | 11/1976 | Flom et al. | 351/205 |
| 4,059,348 | 11/1977 | Jernigan | 351/209 |
| 4,102,564 | 7/1978 | Michael | 351/209 |
| 4,493,539 | 1/1985 | Cannon, Jr. | 351/205 |
| 4,541,697 | 9/1985 | Remijan | 351/211 |
| 4,660,945 | 4/1987 | Trachtman | 351/203 |
| 4,673,265 | 6/1987 | Hache et al. | 351/217 |
| 4,676,611 | 6/1987 | Nelson et al. | 128/731 |
| 4,697,598 | 10/1987 | Bernard et al. | 128/731 |
| 4,706,686 | 11/1987 | Levinson | 351/237 |
| 4,798,456 | 1/1989 | Enoch et al. | 351/246 |
| 4,838,684 | 6/1989 | Smith | 351/239 |
| 4,850,691 | 7/1989 | Gardner et al. | 351/211 |
| 4,861,154 | 8/1989 | Sherwin et al. | 351/205 |
| 5,180,907 | 1/1993 | Udden et al. | 250/205 |
| 5,321,445 | 6/1994 | Fossetti | 351/203 |
| 5,410,376 | 4/1995 | Cornsweet et al. | 351/210 |
| 5,490,098 | 2/1996 | Kardon | 364/589 |
| 5,619,291 | 4/1997 | Putnam | 351/239 |

*Primary Examiner*—Huy Mai
*Attorney, Agent, or Firm*—James Creighton Wray; Meera P. Narasimhan

[57] ABSTRACT

A method for testing the visual capacity of a test subject, the method including the steps of positioning the test subject relative to a visual display; exhibiting to the test subject at least one visual target in the visual display; and monitoring the reaction of the test subject in response to the visual target.

30 Claims, 6 Drawing Sheets

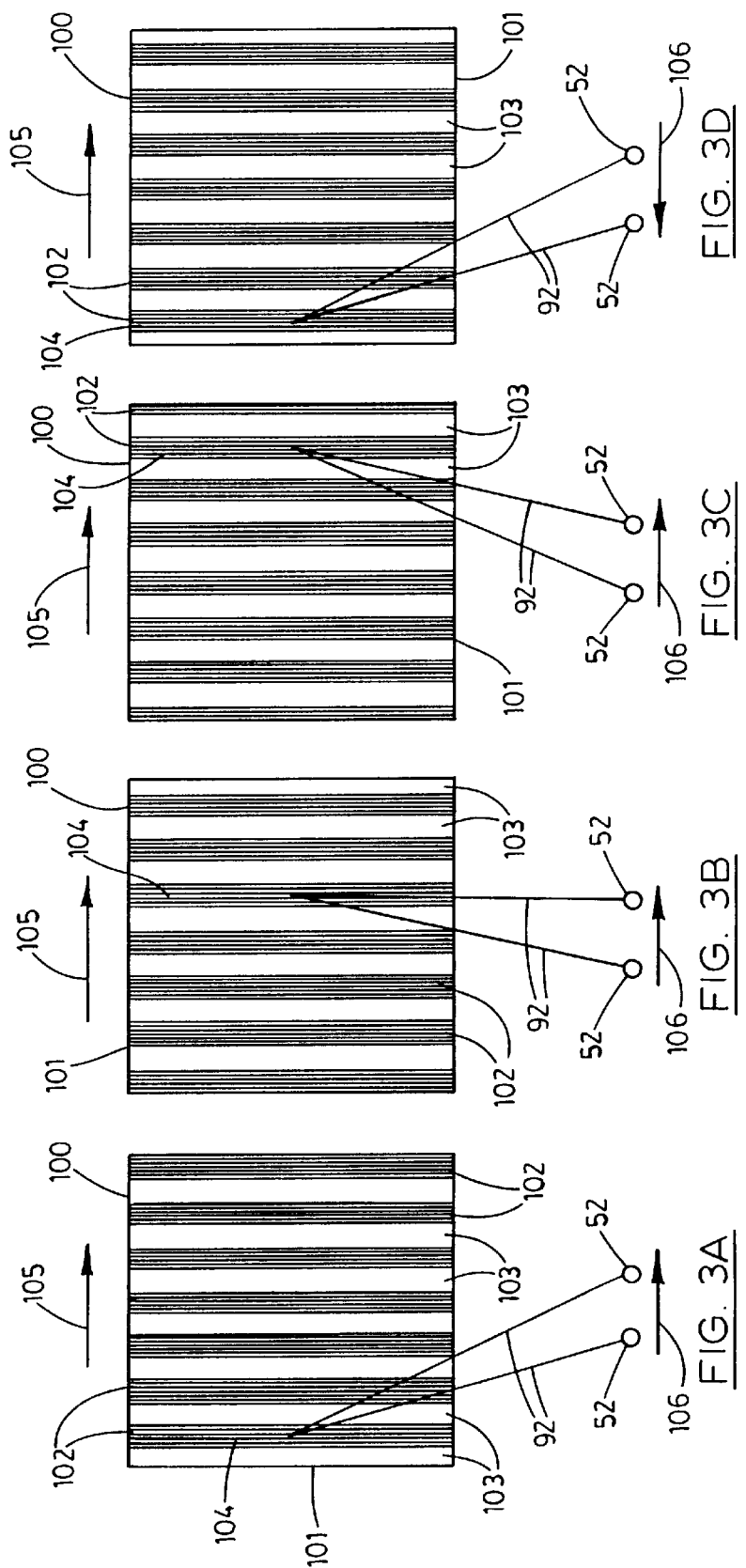

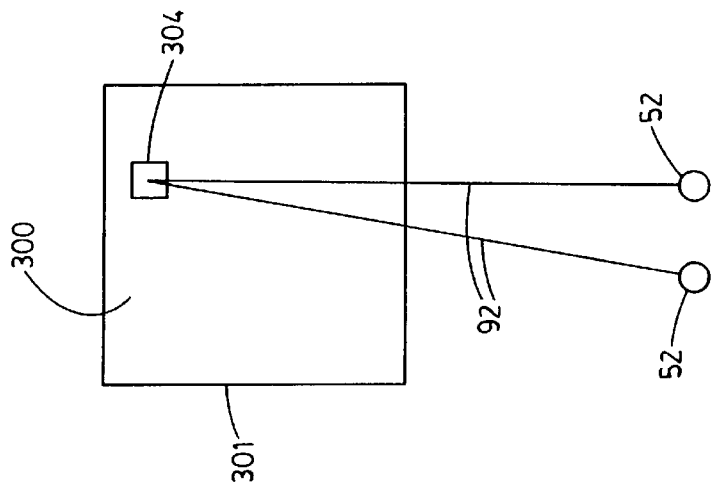
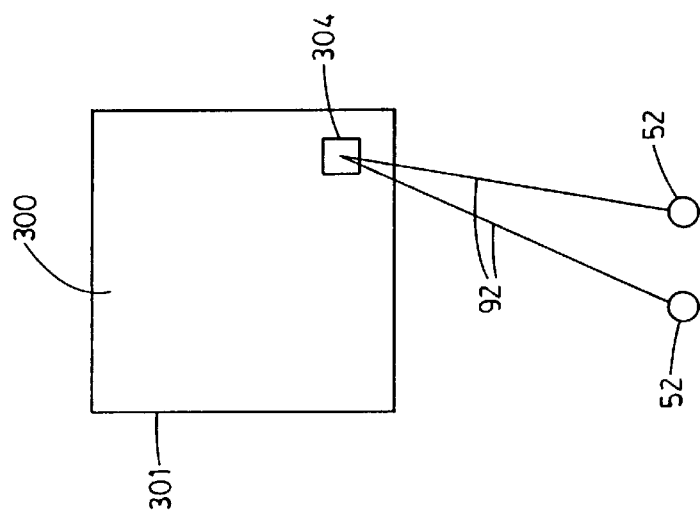
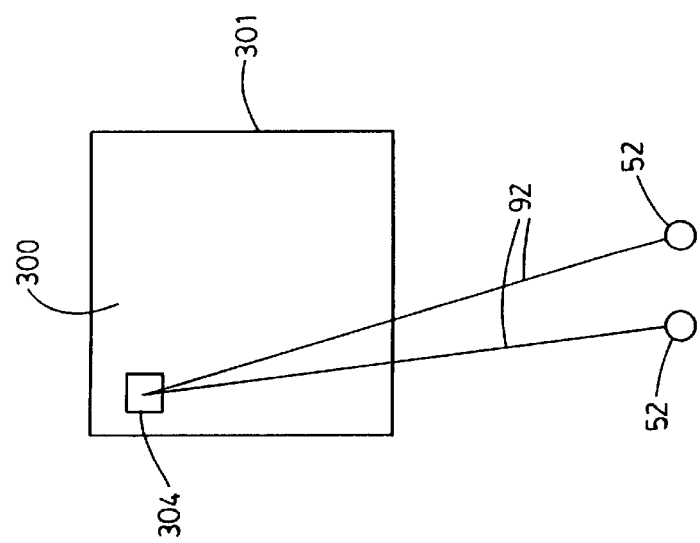

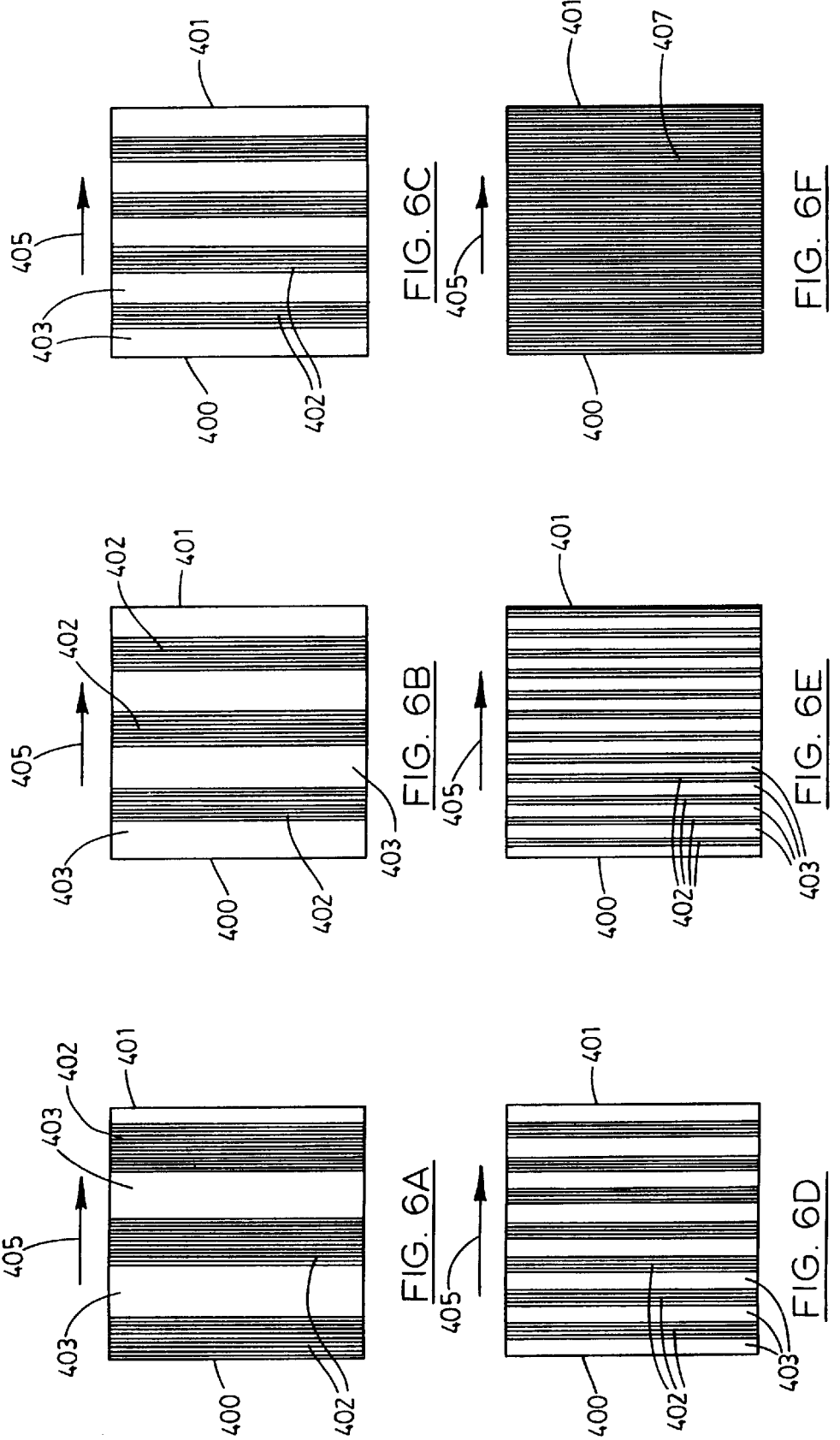

METHOD FOR SUBSTANTIALLY OBJECTIVE TESTING OF THE VISUAL CAPACITY OF A TEST SUBJECT

BACKGROUND OF THE INVENTION

1. Field of the Invention

The present invention relates to a method for testing visual capacity and, more particularly, to such a method which is particularly well suited to determining, on an objective basis, the visual acuity of a test subject for a multiplicity of different purposes.

2. Description of the Prior Art

It has long been known that the visual capacity of human beings, as well as animals and other living creatures, is of significance in a variety of different respects. A determination in this regard may be useful for a multiplicity of different purposes. For example, the visual acuity of a test subject may be of importance in itself, or may be indicative of other physical conditions, capabilities, potential capabilities, and the like. For hundreds of years, it has been known to test the visual acuity of human beings and, based upon the determinations made during the tests, to provide corrective means for improving the visual acuity of the people who were the subjects of the tests. Over the centuries, both the reliability of the tests and the capability for providing correction have, in general, improved.

However, it has similarly long been recognized that the reliability of such tests is influenced by a host of different factors not directly related to the actual visual acuity of the test subject. For example, the tests themselves may inherently be unreliable. The tests may be subject to influence, or the introduction of error, by the person conducting the test. The test subject may be influenced in one way or another to endeavor to distort the test results to indicate greater or lesser visual acuity. Other physical conditions of the test subject may have a bearing, or may otherwise influence, the test results. For example, where neurological or emotional disorders exist in the test subject, the test results may be influenced. The test subject may be too young or too old, or may not have adequate language skills to be able to communicate sufficiently well for reliable results to be obtained. In other cases, the test subject may be other than a human being, such as where the test subject is an animal. All of these and many other circumstances may cause prior art visual tests to be compromised to the extent that the results are partially, or wholly, unreliable.

For these and other reasons, it has long been recognized that the creation of an objective test for the visual capacity of a test subject would, in most respects, have significantly more value than the prior art subjective tests which may be compromised by all of the deficiencies heretofore set forth. Thus, for example, the work of Purkinje and of von Helmholtz in the nineteenth century and of others noted the value of such objective tests for visual capacity. More specifically, it has previously been recognized that an objective physical response identified scientifically as "reflex optokinetic nystagmus" is an involuntary reaction to certain stimuli, including visual stimuli. This reaction occurs in all human beings, as well as in animals, and other living creatures. One example of a common environmental circumstance in which this involuntary physical response occurs is where the field of vision of the subject is intersected by a plurality of visual targets moving at a rate of speed through the field of vision which involuntarily causes the eyes to detect and follow one of the visual targets. The eyes involuntarily follow the selected visual target and, upon that target moving sufficiently laterally within the field of vision, the eyes involuntarily travel in a return direction and detect and follow a succeeding visual target until that visual target, in turn, reaches the lateral edge of the field of vision. This process is repeated continuously for as long as the focus of attention is on the visual targets. A common specific example of this phenomenon is the involuntary reaction of the eyes watching telephone poles being passed while traveling in an automobile or a train, for example.

The physiological explanation for the existence of reflex optokinetic nystagmus involves the mechanisms designed to move the directional axes of the eyes to align the most discriminatory receptor elements, or more specifically the cones of the fovea, with whatever is being visualized, or may need to be visualized. These motions of alignment involve the rotary muscles of each eye, synchronized with its fellow eye, as well as the eyelids, the neck, the shoulders and the entire body of the subject, if the circumstances evoke such a response. Most of these motor functions are normally voluntary, but when involved as a defense mechanism they are involuntary and thus unavoidable.

For example, an unexpected sound or glimpse of an object laterally within the field of vision will cause a rapid reflex turning to the side at which the stimulus is detected. The eyes turn to the limit of visibility in that direction. The eyelids lift for full and unobstructed vision. The neck turns in that direction, as do the shoulders, and, if necessary, the trunk, the legs and the feet of the subject. This same basic response occurs in animals and other living creatures. The apparent biological purpose for this physical response is for the creature to detect and face a possible danger and to afford the optimum visualization of that danger. To reiterate, these responses are involuntary in the circumstances described.

Another physiological consideration having a bearing upon the subject invention is "visual acuity." Visual acuity refers to the ability of an eye to resolve details of form. This is generally measured as the minimal angular separation, in fractions of minutes, of two lines which are just resolvable by the eye as separate. Prior art devices, which have been dependent upon these physiological mechanisms, include the Snellen type visual acuity device. Other typical examples of such a prior art devices include a cylinder which is inscribed with stripes. In use, the device is rotated in the field of vision of the test subject to cause reflex optokinetic nystagmus to occur. A wide variety of other types of devices have also been developed. They are, typically, clumsy and unreliable hand held devices, or complex and expensive mechanical devices. In both cases, such prior art devices are so deficient as to be largely without significant practical value.

Therefore, it has long been known that it would be desirable to have a method for testing visual capacity which reliably permits the objective testing of a test subject; which has application to human beings, animals and other forms of life; which achieves a degree of reliability significantly enhanced over that heretofore achieved in the art; which can be employed for the purpose of directly testing the visual acuity of the test subject as well as testing for a multiplicity of other physical conditions that may be evidenced, or otherwise evaluated, based on the visual acuity of the test subject; which can be employed, more generally, in a multiplicity of environments wherein it is desirable, or of importance, to know what the visual acuity is of the test subject without compromise or influence by subjective considerations; which is comparatively inexpensive to employ while being adaptable to virtually all operative environments; and which is otherwise entirely suited to achieving its operational objectives.

SUMMARY OF THE INVENTION

Therefore, it is an object of the present invention to provide an improved method for testing visual capacity.

Another object is to provide such a method which provides a substantially more reliable method for determining the visual capacity of a test subject than has heretofore been possible.

Another object is to provide such a method which constitutes an entirely objective, as opposed to a subjective, means by which the visual capacity of a test subject can be determined.

Another object is to provide such a method which can be employed on virtually any test subject including human beings, animals and other living creatures, possessing a field of vision and responding thereto.

Another object is to provide such a method which can be employed for a multiplicity of different specific objectives which may be directly or indirectly related to the visual capacity of the test subject, but which may nonetheless be revealed through the practice of the method of the present invention.

Another object is to provide such a method which can be employed in a multiplicity of different operative environments and which may succeed in providing reliable test results notwithstanding countervailing influences such as the environment, the circumstances of conducting the test, the influences of the test subject, or the influences of the person performing the test.

Another object is to provide such a method which can readily be performed with relatively little training and in an efficient fashion to provide reliable test data useful for a wide variety of different purposes.

Another object is to provide such a method which is fully compatible with existing methods and techniques for diagnosing and treating physical conditions in accordance with proper medical practice.

Still another object is to provide such a method which is readily adaptable to specific embodiments directed to particular operational objectives without departing from the invention and without diminishment of the reliability to which the invention is directed.

These and other objects and advantages of the present invention are achieved, in the preferred embodiment of the present invention, in a method for testing the visual capacity of a test subject, the method comprising the steps of positioning the test subject relative to a visual display; exhibiting to the test subject at least one visual target in the visual display; and monitoring the reaction of the test subject in response to the visual target.

BRIEF DESCRIPTION OF THE DRAWINGS

FIGS. 3A, 3B, 3C and 3D illustrate a first embodiment of the visual display employed in the practice of the method of the present invention.

FIGS. 5A, 5B and 5C illustrate a third embodiment of the visual display employed in the practice of the method of the present invention.

FIGS. 6A, 6B, 6C, 6D, 6E and 6F illustrate a fourth embodiment of the visual display employed in the practice of the method of the present invention.

DESCRIPTION OF THE PREFERRED EMBODIMENT

Figure 1:
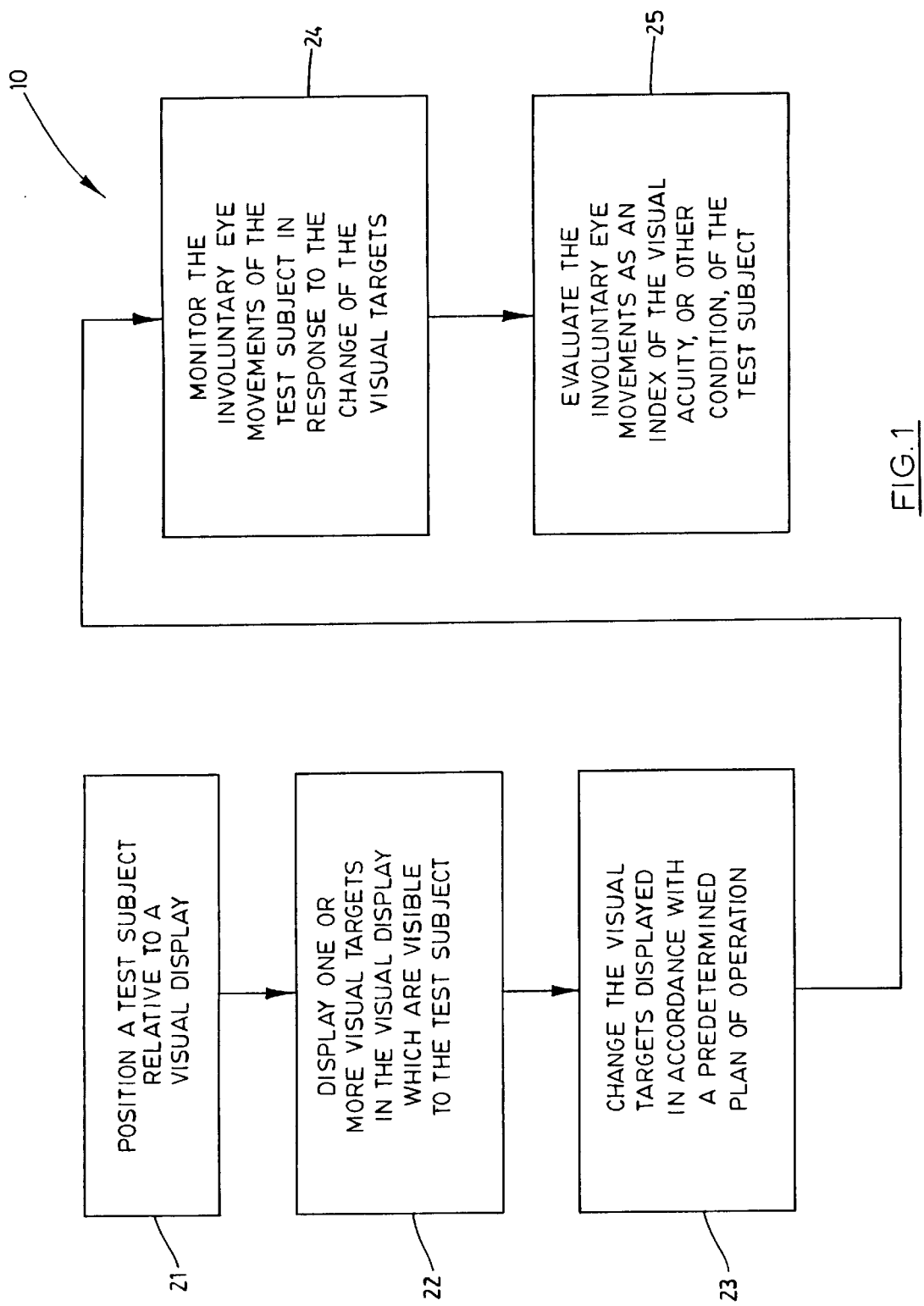
FIG. 1 is a schematic diagram of the steps of the preferred embodiment of the method of the present invention.

Referring more particularly to the drawings, the method of the present invention is generally indicated by the numeral 10 in FIG. 1.

For purposes of illustrative convenience and a general identification of the steps of the preferred embodiment of the method of the present invention, FIG. 1 illustrates the basic steps of the method in a schematic diagram. As shown therein, the first step is generally indicated by the numeral 21. The first step provides that a test subject be positioned relative to a visual display, as will hereinafter be described in greater detail. The second step of the method is generally indicated in FIG. 1 by the numeral 22. The second step provides, generally, for displaying one or more visual targets in the visual display which are visible to the test subject. The third step of the method of the present invention is generally indicated by the numeral 23 in FIG. 1. The third step calls for a change in the visual targets displayed in accordance with a predetermined plan of operation, as will hereinafter be discussed in greater detail. The fourth step of the method of the present invention is generally indicated by the numeral 24 in FIG. 1. The fourth step, in general, calls for the person practicing the method hereof to monitor the involuntary eye movements of the test subject in response to the change of the visual targets. The fifth step of the method of the present invention is generally indicated by the numeral 25 in FIG. 1. The fifth step, in general, calls for the person performing the method to evaluate the involuntary eye movements of the test subject as an index of the visual acuity, or other condition, of the test subject.

It will be understood that, depending upon the particular purpose for the practice of the method, the condition of the test subject, the information desired from the practice of the method, and a host of other considerations, the steps in the method may vary from the foregoing. Similarly, it will be understood that the specific details of each of the steps of the method can be varied depending upon the same considerations and additional steps included, all within the scope of the method of the present invention. This will hereinafter become more clearly apparent.

Figure 2:
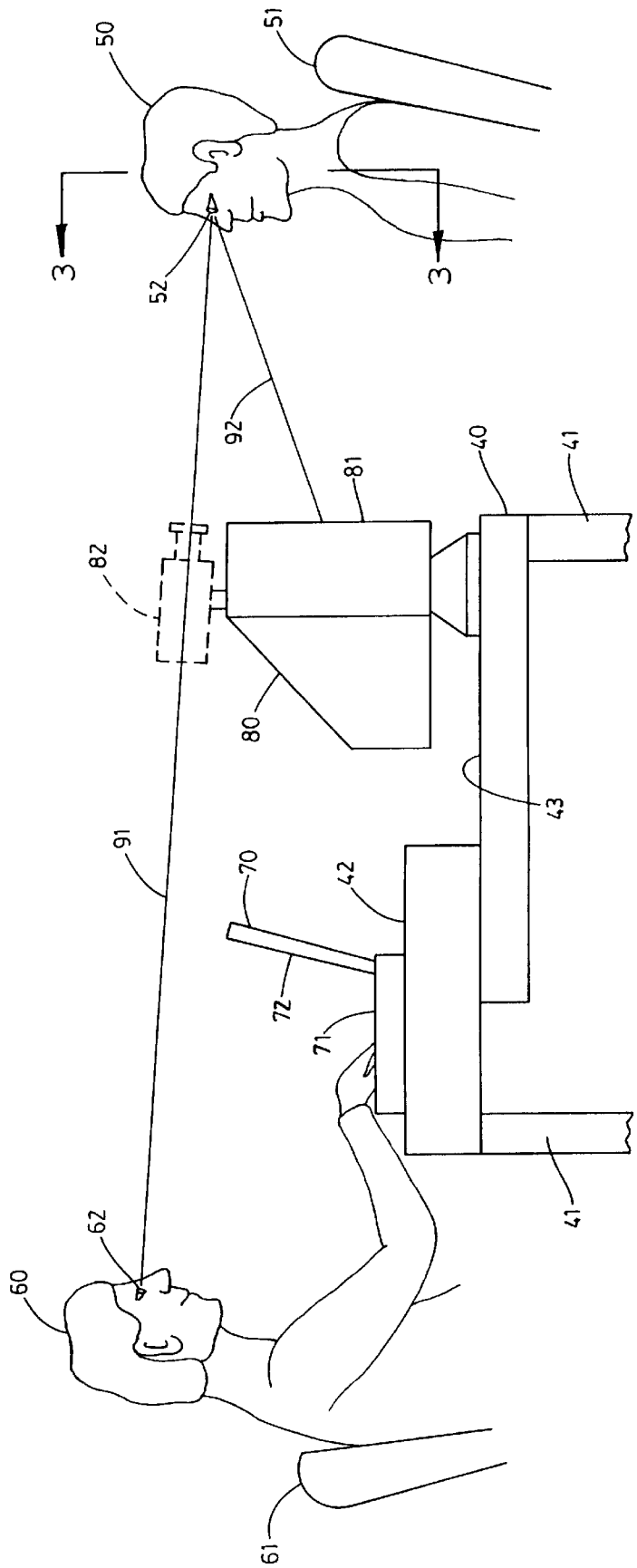
FIG. 2 is a fragmentary side elevation illustrating a typical operative environment within which the method of the present invention can be preformed and depicting a test subject on the right and an operator on the left.

Depicted for illustrative convenience in FIG. 2 is a typical operative environment for the practice of the method of the present invention. The illustration of FIG. 2 is intended only to illustrate one such operative environment. As will subsequently be discussed in greater detail, a variety of operative environments can be employed, suited both to the preferences of the operator, as well as to the circumstances and purposes for practice of the method of the present invention. As shown in FIG. 2, a table or other means of support is generally indicated by the numeral 40 and has four (4) legs 41 which support the table on a supporting surface, not shown. The table itself has a first support surface 42 which is substantially horizontal and a lower secondary, or second, support surface 43 which is also horizontal, but which is vertically below the first support surface.

As shown in FIG. 2, a test subject is indicated by the numeral 50, seated in a chair 51 facing from right to left. For purposes of illustrative convenience, the eyes of the test subject are generally indicated in FIG. 2 and in other views by the numerals 52. An operator, or person, practicing the method of the present invention is generally indicated in FIG. 2 by the numeral 60. The operator 60 is seated in a chair 61. The eyes of the operator practicing the method are generally indicated by the numeral 62. Again, as illustrated in the environment shown in FIG. 2, the operator 60 has a computer 70 having a keyboard 71 and a screen 72 which is visible to the operator.

A display device, monitor, or television is generally indicated by the numeral 80. The display device can be any means by which the visual display hereinafter discussed can be exhibited to the test subject, such as for example, a television, a computer screen, a projected image or the like. Similarly, the visual display can be exhibited to the test subject at any distance from the test subject consistent with the plan of operation. Thus, for example, the visual display in the environment of FIG. 2 could be projected on a screen behind the operator, but within the field of vision of the test subject.

The television 80 is mounted in upright relation on the second support surface 43 of the table 40 and has a screen 81 directly facing and visible by the test subject 50. As shown in phantom lines in FIG. 2, a sensing device 82 is mounted on the television or supported in the position shown therein by any other means. A variety of types of sensing devices 82 can be employed for the purpose such as appropriate models of the "dual-Purkinje-image (DPI) Eye-tracker" manufactured by Fourward Optical Technologies, Inc.

Still further, referring to FIG. 2, a first line of sight 91 extends between the eyes 62 of the operator 60 and the eyes 52 of the test subject 50. A second line of sight 92 extends from the eyes 52 of the test subject 50 and the screen 81 of the television 80. The first and second lines of sight are employed herein for illustrative convenience in depicting the relative positions and relationships between the operator, test subject and television screen.

Referring to FIGS. 3A, 3B, 3C and 3D, a visual display 100 is shown by the television 80 on the screen 81 thereof and is visible to the test subject 50 is depicted in each of the views. As shown therein, FIGS. 3A, 3B, 3C and 3D depict a sequence of visual images occurring in rapid sequence starting with the image in FIG. 3A and continuing through the image of FIG. 3D. As noted, the sequence of images is continuous and is merely represented herein by the four (4) sequential depictions of FIGS. 3A, 3B, 3C and 3D. For purposes of understanding the speed with which these images move, it will be understood that the period of time elapsing between the image of FIG. 3A and the image of FIG. 3D is typically measured in millimeters per second.

The visual display 100 has a rectangular margin 101 constituting the border or boundary of the screen 81 of the television 80. The visual display has a plurality of vertical bars 102 extending from the lower edge of the margin 101 to the upper edge of the margin. Adjacent vertical bars are spaced from each other a distance equal to the width of each of the vertical bars. The spaces between the vertical bars are indicated by the numeral 103. For purposes of illustrating the practice of the method of the present invention, a visual target is indicated by the numeral 104 in each of the views of FIGS. 3A through 3D constituting the vertical bar which attracts the attention of and is followed by the eyes 52 of the test subject along the second lines of sight 92. Again for purposes of more clearly illustrating the operation of the visual display and the practice of the method of the present invention, arrow 105 indicates the direction of movement of the vertical bars 102 in the visual display. Similarly, arrow 106 indicates the direction of movement of the eyes 52 of the test subject and, thus, the second lines of sight 92.

Figure 4B:
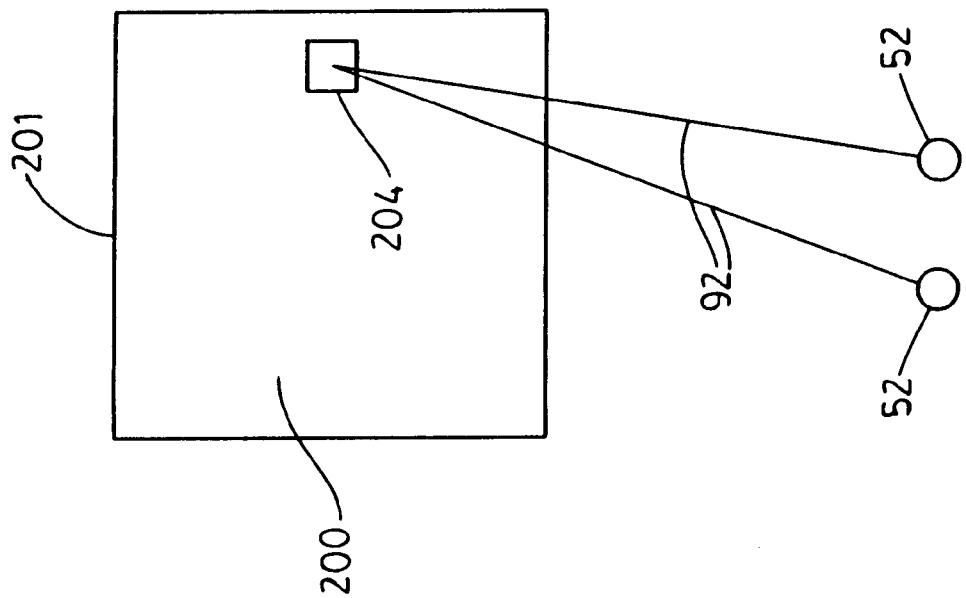
FIGS. 4A and 4B illustrate a second embodiment of a visual display employed in the practice of the method of the present invention.
Figure 4A:
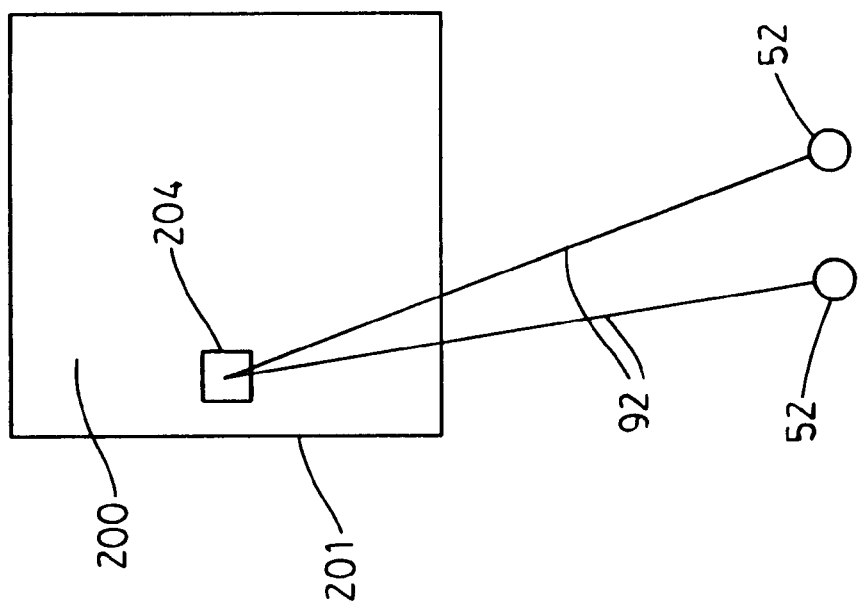

A second embodiment of the method of the present invention is depicted in FIGS. 4A and 4B. As shown therein, a visual display is indicated by the numeral 200, again representing the image shown on the screen 81 of the television 80 visible to the test subject 50. The visual display has a rectangular margin 201. As shown in FIGS. 4A and 4B, a visual target 204 appears in the visual display, as will subsequently be discussed in greater detail.

FIGS. 5A, 5B and 5C illustrate a third embodiment of the method of the present invention. As shown therein, a visual display 300 represents, again, the image visible on the screen 81 of the television 80 by the test subject 50. The visual display 300 has a rectangular margin 301. A visual target 304 appears in the visual display 300, as will subsequently be discussed in greater detail.

FIGS. 6A, 6B, 6C, 6D, 6E and 6F depict a fourth embodiment of the method of the present invention. As shown therein, a visual display 400 represents the image visible on the screen 81 of the television 80 to the test subject 50. The visual display has a rectangular margin 401. The visual display contains a plurality of vertical bars 402 which, as can be seen in FIGS. 6A through 6F, gradually become more narrow, as well as more numerous, as the visual display progresses from FIG. 6A through FIG. 6F. The vertical bars 402 are separated from each other by spaces 403. It will be seen that in each of the views of FIGS. 6A through 6E, the width of each of the vertical bars is the same as the width of the space between the adjacent vertical bars. In each of the views of FIGS. 6A through 6F, arrow 405 indicates the direction of movement of the vertical bars in the visual display. Referring more particularly to FIG. 6F, the visual display depicts a solid black surface 407 which is, in reality, a visual image containing such a prolixity of vertical bars that the human eye cannot any longer detect the individual vertical bars, but rather see the visual display as a solid black surface. Again, for illustrative convenience, it will be understood that the period of time elapsed in the progression of the visual display from FIG. 6A to FIG. 6F is measured in millimeters per second.

As heretofore noted, the method of the present invention is adapted to be employed for a multiplicity of different purposes based upon making an objective determination as to the visual capacity of the test subject, whether that test subject is a human being, an animal, or another living creature. Since the method is an objective test, it does not require, nor is it necessarily benefitted by, having any comments or observations from the test subject. This is, of course, particularly of benefit where the test subject may be an animal and unable to provide such subjective information.

Furthermore, the reason for conducting the test may not necessarily be to determine solely the visual capacity or acuity of the test subject. Reaching a determination as to the visual capacity or acuity of the test subject may be indicative of other physical conditions and therefore of benefit in diagnosing or treating a variety of physical conditions.

Still further, the specific embodiment of the test conducted in the practice of the method of the present invention can be varied as well as conducted in multiple embodiments for purposes of providing the objective data desired. Thus, the specific series of tests conducted are selected in accordance with a plan of operation tailored to the specific objectives desired to be achieved. The results of the tests can, for example, be useful in determining the spacial acuity, temporal acuity, contrast sensitivity, color discrimination and flicker fusion frequency of the test subject. Since the reaction of the test subject is entirely involuntary and cannot be artificially produced, or in other words faked, the results are reliable beyond anything that has heretofore been achieved in the art.

Referring then more particularly to the drawings as illustrating several representative embodiments of the method of the present invention, the test subject 50 is seated in the chair 51, as shown in FIG. 2, facing the operator 60 as well as the screen 81 of the television 80. The operator 60, seated in the chair 61 thus has a line of sight 91 between the operator's eyes 62 and the test subject's eyes 52. The test subject has a line of sight 92 to the screen 81 of the television 80. The sensing device 82 can be used to monitor the eye movements of the eyes 52 of the test subject without the operator 60 doing so, or in combination with monitoring by the operator. Alternatively, the operator can monitor the test subject's eye movement without using the sensing device.

As previously discussed, the computer 70, operated by the operator 60, is linked in controlling relation to the television 80 using appropriate software. By sending appropriate commands using the keyboard 71, the operator can control the visual display exhibited on the screen 81 of the television 80. Preferably, the screen 72 of the computer 70 displays precisely what is displayed in the visual display of the television, as well as showing the measured dynamics, results and other data that may be of assistance to the operator during practice of the method. These capabilities and details can be tailored to suit proscribed operating parameters for predetermined operative environments, as well as, more specifically, to suit the preferences of the operator within the parameters of the environment of use.

Referring then to the embodiment of the visual display 100 shown in FIGS. 3A through 3D as illustrative of the practice of the method of the present invention, the operator 60 operates the television 80 to display the images shown in FIGS. 3A through 3D. The vertical bars 102 are moved from left to right in the visual display at a speed sufficient to cause reflex optokinetic nystagmus by the test subject, as previously defined. Thus, using FIG. 3A as an example, the vertical bars 102 are moved at a fairly rapid speed from left to right in the visual display 100 in the direction indicated by arrow 105. The test subject's eyes 52, in accordance with this physical phenomenon, are attracted to one of the vertical bars 102 which thereby becomes the visual target 104. The eyes 52 of the test subject involuntarily track the visual target 104 as it travels across the screen 81 in the visual display 100 from left to right. This is shown in FIGS. 3A, 3B and 3C. When the selected visual target 104 travels off the screen to the right and thus from the visual display 100, the eyes 52 of the test subject involuntarily return to the left, select and track a second visual target 104, as depicted in FIG. 3D. The eyes of the test subject continue to follow that second visual target as the visual target travels from left to right in the visual display until it passes from the visual display off the screen to the right. The eyes of the test subject then again involuntarily return to the left, select and track another visual target 104. This sequence of operation is repeated for a sufficient length of time for the operator to make the desired determinations.

During the performance of this operation, the visual display 100, and more particularly the vertical bars 102, are varied in some respect in accordance with the plan of operation of the operator. Typically, such variation is of a type which causes the vertical bars to become more difficult to see. Such variables include changing the speed of movement of the vertical bars, changing the color of the vertical bars, changing the shading of the vertical bars, changing the contrast of the vertical bars with the background in the visual display, or more specifically the spaces 103 between the vertical bars, changing the widths of the bars and the spaces therebetween and in any other respects that may be deemed desirable in accordance with the plan of operation. Similarly, these variables can be performed in combination, again depending upon the plan of operation. It is, however, preferred that the widths of the bars and the spaces therebetween be the same width. As the test continues and with the variation in the visual display as discussed, the operator continues to monitor either individually and/or with the sensing device 82 the reflex optokinetic nystagmus. At some point, again depending upon the plan of operation, the eyes 52 of the test subject can no longer locate and track the vertical bars, thus indicating that the limit of visual acuity has been reached. This information is recorded by the operator, either using the computer 70 and/or by any other convenient means. This data is then used to determine objectively the visual acuity of the test subject for the particular purpose desired.

The embodiment of the method of the present invention shown in FIGS. 3A through 3D can be varied in a wide variety of respects. For example, in addition to the use of any combination of the variables previously set forth, the test can be conducted in reverse. More specifically, the visual display 100 can be initiated with the variables purposely used in such a manner as to preclude the eyes 52 of the test subject 50 from seeing the vertical bars 102, or from having the reflex optokinetic nystagmus phenomenon occur. In this embodiment of the practice of the method of the present invention, the test subject continues to watch the visual display 100 on the screen 81 of the television 80 while the operator 60 gradually adjusts the a variables in whatever combination correspond to the plan of operation. The variables are adjusted in such a manner that the vertical bars gradually become more distinguishable, or visible, to the test subject and until the reflex optokinetic nystagmus phenomenon begins to occur. At this point, the operator notes that this phenomenon has taken place and therefore makes a determination as to the visual acuity of the test subject.

The evaluation of the involuntary eye movements of the test subject can be employed to provide an index of the visual acuity, or other condition of the test subject. Conventional or other methods, can then be employed to interpret the test data. Conventional methods include making comparisons to the Ishihara color plate standards, the contrast sensitivity standards, the standards for flicker fusion frequencies, and the like.

The embodiment of the invention shown in FIGS. 4A and 4B can also be employed in a variety of different specific embodiments depending upon the plan of operation. The test subject 50 is again seated, as heretofore described and shown in FIG. 2, watching the visual display 200 on the screen 81 of the television 80. Under the control of the operator 60 using the computer 70, the visual target 204, in one specific embodiment, is caused to appear and disappear within the visual display appearing randomly at various locations within the visual display. Again, the eyes 52 of the test subject involuntarily move to each successive new location of the visual target 204 when visualized. This is an involuntary reaction which is thus monitored by the operator 60 with or without the assistance of the sensing device 82.

Again, the operator employs the same types of variables in changing the visual target 204 until the eyes 52 of the test subject can no longer see and track the visual target. Thus, the visual target may be changed in size, speed of appearance and disappearance, color, contrast, shading and the like, in accordance with the plan of operation. Similarly, as with the prior embodiment of the method of the present invention, the test can be conducted in reverse wherein the variables are first adjusted in such a manner so that the eyes 52 of the test subject cannot see the visual target. Subsequently, over time and as the test subject continues to watch the visual display 200, the variables are adjusted until the eyes 52 of the test subject can see the visual target. When the eyes 52 begin to follow the visual target, the operator notes this fact in relation to the criteria set forth.

The embodiment of the method of the present invention shown in FIGS. 5A, 5B and 5C provides for the visual display 300 to contain the visual target 304 which is moved within the visual display, but is not caused to appear and disappear. The visual target 304 is moved at a speed which is followed by the eyes 52 of the operator until the visual target can no longer be resolved by the eyes 52 of the test subject. Again, the variables previously identified are employed to cause the visual target 304 to become less visible to the eyes of the test subject in accordance with the plan of operation. When the eyes of the test subject can no longer resolve the visual target, such involuntary eye movement stops and the operator notes this fact in accordance with the criteria established. As with the other embodiments, this specific embodiment of the method of the present invention can be performed in reverse by beginning performance of the test with the visual target 304, not visible to the eyes 52 of the test subject, and the variable subsequently adjusted over time in such a manner that the visual target ultimately becomes visible. When involuntary eye movements of the test subject begin, the operator notes this relative to the criteria set forth.

The embodiment of the present invention shown in FIGS. 6A through 6F can also be employed in a variety of specific ways. In one specific example, the vertical bars 402 are moved from left to right in the visual display 400, as indicated by the arrow 405. As the vertical bars are moved, their width and the width of the spaces between the bars is reduced so that, in effect, more and more vertical bars are visible in the visual display as such operation continues. This is continued until the eyes 52 of the test subject can no longer distinguish or resolve the vertical bars and the visual display 400 becomes, in effect, a solid or black surface as depicted in FIG. 6F. At this point, the eyes 52 of the test subject stop moving and this fact is noted by the operator 60 as previously discussed.

As with the other specific embodiments of the method of the present invention, the method of the invention shown in FIG. 6A through FIG. 6F can be preformed in reverse. The visual display at the time of initiation is as depicted in FIG. 6F. Over time, the widths of the vertical bars 402 and the spaces 403 between the vertical bars enlarge until the eyes 52 of the test subject can first resolve the vertical bars. At this point, involuntary eye movement begins which is noted by the operator 60.

A still further embodiment of the method of the present invention, illustrated in FIGS. 6A through 6F, involves movement of the vertical bars at a greater and greater rate of speed from left to right in the visual display 400, as indicated by arrow 405. As the speed is increased, the moving targets ultimately become beyond the capability of the eyes 52 of the test subject to resolve. At this point, they appear to fuse, or become a solid surface, as depicted in FIG. 6F. When this occurs, involuntary eye movement ceases which is noted by the operator 60. The phenomenon is known as "flicker fusion."

Therefore, the method for testing visual capacity of the present invention reliably permits the objective testing of the visual capacity of a test subject; has application to human beings, animals and other forms of life; achieves a degree of reliability significantly enhanced over that heretofore achieved in the art; can be employed for the purpose of directly testing the visual acuity of the test subject as well as for a multiplicity of other physical conditions that may be evidenced or otherwise evaluated based on the visual acuity of the test subject; can be employed, more generally, in a multiplicity of environments wherein it is desirable, or of importance, to know what the visual acuity is of the test subject without influence by subjective considerations; is comparatively inexpensive to employ while being adaptable to virtually all operative environments; and is otherwise entirely suited to achieving its operational objectives.

Although the invention has been herein shown and described in what is conceived to be the most practical and preferred embodiment, it is recognized that departures may be made therefrom within the scope of the invention which is not to be limited to the illustrative details disclosed.

Having described my invention, what I claim as new and desire to secure by Letters Patent is:

1. A method for substantially objective testing of the visual capacity of a test subject, the method comprising the steps of positioning the test subject relative to a visual display; presenting to the test subject at least one visual target in said visual display; and monitoring the substantially involuntary reaction of the test subject in response to said visual target.

2. The method of claim 1 wherein said presenting step includes moving the visual target within said visual display.

3. The method of claim 2 wherein said moving in the presenting step is performed in accordance with a predetermined plan of operation.

4. The method of claim 1 wherein said presenting step includes causing the visual target to appear and disappear within said visual display.

5. The method of claim 4 wherein said causing of the presenting step is performed in accordance with a predetermined plan of operation.

6. The method of claim 1 wherein said presenting step includes varying the contrast of the visual target within said visual display.

7. The method of claim 6 wherein said varying is performed in accordance with a predetermined plan of operation.

8. The method of claim 1 wherein said presenting step includes varying the color of the visual target within said visual display.

9. The method of claim 8 wherein said varying is performed in accordance with a predetermined plan of operation.

10. A method for substantially objectively testing of the visual capacity of a test subject, the method comprising the steps of positioning the test subject relative to a visual display; presenting to the test subject at least one visual target in said visual display; and monitoring the substantially involuntary reaction of the test subject in response to said visual target and wherein said presenting step is performed so as to cause involuntary movement of at least one eye of said test subject and the monitoring step includes detecting said involuntary movement of said eye as an index of the visual acuity of the eye.

11. The method of claim 10 wherein, in said presenting step, said visual target is caused to appear in said visual display in such a manner as to stimulate the retina of said eye to cause involuntary movement of the eye, for at least an instant, to the visual target.

12. The method of claim 11 wherein, in said presenting step, said visual target is caused to appear in said visual display by varying the visual target within said visual display in at least one of the variables selected from the group consisting of motion, position, size, color, contrast, intensity, hue or other variant.

13. The method of claim 12 wherein, in said presenting step, said varying by motion is performed by changing the direction of said motion and/or the speed of said motion.

14. The method of claim 12 wherein, in said presenting step, said varying by position is performed by causing the visual target randomly to change position and/or periodically to appear and disappear in said visual display.

15. The method of claim 12 including the step of interpreting said involuntary movement of the eye, in response to the visual target, in an effort to determine said visual acuity of the eye.

16. The method of claim 12 including the step of interpreting said involuntary movement of the eye, in response to the visual target, in an effort to determine a predetermined physical condition of the test subject using the test subject's visual acuity as an index thereof.

17. A method for testing the visual capacity of a test subject for a predetermined purpose, the method comprising the steps of:

A. positioning a test subject in a predetermined position so that the test subject's field of vision with the test subject's eyes is in a predetermined direction;

B. placing a visual display at a predetermined position relative to the test subject and within said field of vision of the test subject;

C. positioning a monitor relative to said test subject so that said monitor can detect the movements of the test subject's eyes;

D. presenting at least one visual target within said visual display;

E. varying said visual target within said visual display in accordance with a predetermined plan of operation and in such a manner as to cause involuntary movement of the eyes of the test subject in response to said varying of the visual target within the visual display;

F. detecting said involuntary movement of the eyes of the test subject; and

G. interpreting said involuntary movement of the eyes of the test subject, as detected in said detecting step, in an effort to determine the visual acuity of the eyes of the test subject.

18. The method of claim 17 wherein said monitor of step C. is a human operator, who has a line of sight coinciding with the eyes of the test subject, and the detecting step is performed by said human operator observing and recording the results of said detecting step.

19. The method of claim 18 wherein the varying step is performed by a computer system linked in controlling relation to said visual display.

20. The method of claim 19 wherein, in said varying step, said varying is controlled by said human operator operating said computer system.

21. The method of claim 20 wherein said computer system has a secondary visual display visible to the human operator and which displays the same image as the visual display viewed by the test subject.

22. The method of claim 17 wherein said monitor of step C. is a nonhuman sensor capable of registering said involuntary eye movement of the test subject and the detecting step performed by said nonhuman sensor.

23. The method of claim 17 wherein said detecting step is performed by a nonhuman sensor; said monitor of step C. is a human operator; and the varying step is performed by a computer system linked in controlling relation to said visual display and under the control of the human operator.

24. The method of claim 17 wherein, in said varying step, the visual target includes a plurality of lines moved in a predetermined direction within the visual display at a speed at least sufficient to cause said involuntary movement of the eyes of the test subject.

25. The method of claim 17 wherein, in said varying step, the visual target repeatedly appears and disappears in said visual display in random positions at a speed at least sufficient to cause said involuntary movement of the eyes of the test subject.

26. The method of claim 17 wherein, in said varying step, the visual target moves randomly to different positions in said visual display at a speed at least sufficient to cause said involuntary movement of the eyes of the test subject.

27. The method of claim 17 wherein, in said varying step, the visual target includes a plurality of lines moved in a predetermined direction in the visual display at a speed at least sufficient to cause said involuntary movement of the eyes of the test subject and wherein said lines have common widths and spacings which are reduced in size over time, as said lines are moved, until said involuntary movement of the eyes of the test subject no longer takes place because the eyes of the test subject can no longer detect said lines.

28. The method of claim 17 wherein, in said varying step, the visual target is varied in size, color, contrast or other variant until said involuntary movement of the eyes of the test subject no longer takes place because the eyes of the test subject can no longer detect said visual target.

29. The method of claim 17 wherein, in said varying step, the visual target is caused to appear and disappear in the visual display at an increasing frequency until said involuntary movement of the eyes of the test subject no longer takes place because the eyes of the test subject can no longer detect said varying.

30. The method of claim 17 wherein, in said varying step, the visual target is caused to appear and disappear in the visual display at a frequency which cannot be detected by the eyes of the test subject and said frequency is gradually reduced until the eyes of the test subject can detect said varying and said involuntary movement of the eyes of the test subject commences as a consequence.

* * * * *